United States Patent [19]
Usui et al.

[11] Patent Number: 5,969,532
[45] Date of Patent: Oct. 19, 1999

[54] METHOD OF INSPECTING CRACK IN CERAMIC SUBSTRATE

[75] Inventors: Minoru Usui, Shiojiri; Takahiro Katakura, Okaya; Takaichi Wada; Motonori Okumura, both of Suwa; Nobuo Takahashi, Owariasahi; Natsumi Shimogawa, Nagoya; Keizo Miyata, Ichinomiya, all of Japan

[73] Assignees: Seiko Epson Corporation; NGK Insulators, Ltd., both of Japan

[21] Appl. No.: 08/841,105

[22] Filed: Apr. 30, 1997

[30] Foreign Application Priority Data

May 9, 1996 [JP] Japan ..................................... 8-114611

[51] Int. Cl.⁶ .................................................. G01N 27/20
[52] U.S. Cl. .......................... 324/557; 324/525; 324/693; 73/799
[58] Field of Search ..................................... 324/500, 525, 324/557, 693, 719; 73/87, 763, 799

[56] References Cited

U.S. PATENT DOCUMENTS

| 3,803,485 | 4/1974 | Crites et al. | 324/693 |
| 4,503,710 | 3/1985 | Oertle et al. | 73/763 |
| 5,378,991 | 1/1995 | Anderson et al. | 324/557 |
| 5,395,641 | 3/1995 | Shibata et al. | 427/8 |

FOREIGN PATENT DOCUMENTS

| 2 304 078 | 10/1976 | France . |
| 2 607 254-A1 | 5/1988 | France . |
| 2 034 898 | 6/1980 | United Kingdom . |

OTHER PUBLICATIONS

Patent Abstracts of Japan—vol. 095, No. 009, Oct. 31, 1995 & JP 07 161570 A (Murata Mfg Co Ltd), Jun. 23, 1995, *abstract*.

Patent Abstracts of Japan—vol. 7, No. 220 (P-226) [1365], Sep. 30, 1983 & JP 58 111749 A (Fuji Latex K. K.), Jul. 2, 1983, *abstract*.

Machine Design, vol. 53, No. 15, 1981, Cleveland, Ohio, U.S., p. 40 XP002038073 Anonymous: "Sponge Probe Pinpoints Pinholes" *the whole document*, Jun. 1981.

*Primary Examiner*—Glenn W. Brown
*Attorney, Agent, or Firm*—Parkhurst & Wendel, L.L.P.

[57] ABSTRACT

A method of inspecting a crack in a ceramic substrate that is not exposed on the surface. The method can detect all cracks and make objective judgement possible by expressing the inspection result as numerical data. Conductors are disposed on both faces of a ceramic substrate, wherein one of the conductors is a conductive liquid; the insulation resistance value or an electric property dependent on the insulation resistance is measured with the conductive liquid or other conductors electrically connected to the conductive liquid which are used as electrodes.

7 Claims, 3 Drawing Sheets

METHOD OF INSPECTING CRACK IN CERAMIC SUBSTRATE

BACKGROUND OF THE INVENTION

1. Field of the Invention

The present invention relates to a method of inspecting any crack in a ceramic substrate, and in particular, a ceramic substrate used in manufacturing a sensor, a resistor element, an actuator for an ink-jet print head, or the like.

2. Description of Related Art

Conventionally, a ceramic substrate coated with a conductive film has been used as an electrode, a resistor, a lead, an output terminal, or the like in a sensor, a resistor element, an actuator for an ink-jet print head, or the like.

As a method of manufacturing a ceramic substrate coated with a conductive film, a method of applying by printing conductive paste on a ceramic substrate is appropriate. This is because a uniform film having a complicated pattern can be efficiently formed and the conductive film can be adjusted to have a wide range of thickness by adjusting the viscosity of the conductive paste.

In order to meet the recent demands for a miniaturized and lightened actuator for an ink-jet print head, or the like., thinning of a ceramic substrate has been carried forward, and recently, a ceramic substrate which is $10 \mu m$ or less in thickness is now available. This is accompanied by a fear that handling of a ceramic substrate in manufacturing may cause a crack in the ceramic substrate. If a ceramic substrate is cracked, not only the mechanical strength of the ceramic substrate is so lowered that it can not be put to practical use, but also leakage of ink may be caused.

As a method of inspecting any crack in a ceramic substrate, conventionally, there are known a red check test, a method of inspection by visual observation or with microscope using liquid penetrant (liquid penetrant test) such as a fluorescent penetrant test, a method of inspection by detecting leakage of gas such as gaseous helium and air, a method using an image processor, etc.

However, the liquid penetrant test suffers from a problem that it depends to a great extent on the skillfulness of the inspector, cracks are likely to be left undetected, and the result of the inspection is difficult to express as numerical data. Further, in case a ceramic substrate applied to, for example, an actuator for an ink-jet print head has a multi-layer functional film formed thereon, there is a problem that, according to the method using liquid penetrant, it takes the liquid penetrant much time to ooze.

The method of inspection by detecting leakage of gas has a problem that, since a closed space is necessary, there is technical difficulty and the scale of the apparatus has to be large.

Further, the method using an image processor has a problem that, depending on the resolution of the apparatus, a microscopic crack may be difficult to detect.

Still further, as a defect common to the conventional methods on the whole, there is a problem that a crack which is, for example, shut by a functional film such as a conductive film and thus, which is not exposed on the surface of a ceramic substrate can not be detected.

SUMMARY OF THE INVENTION

In view of the above, an object of the present invention is to provide a method of inspecting any crack in a ceramic substrate which eliminates the inconveniences mentioned in the above, which detects even a crack that is not exposed on the surface of a ceramic substrate, which does not leave a crack undetected, and which can make objective judgement possible by expressing the result of inspection as numerical data.

According to the present invention, there is provided a method of inspecting any crack in a ceramic substrate which comprises; disposing conductors on both faces of the ceramic substrate, both of the conductors being conductive liquid, and measuring an insulation resistance value between both faces of the ceramic substrate or an electrically characteristic value which depends on the insulation resistance value with the conductive liquid or other conductors electrically connected to the conductive liquid as electrodes.

Further, according to the present invention, there is provided a method of inspecting any crack in a ceramic substrate which comprises; disposing conductors on both faces of the ceramic substrate, one of the conductors being conductive liquid and the other of the conductors having a plane electrically connected portion, and measuring an insulation resistance value between both faces of the ceramic substrate or an electrically characteristic value which depends on the insulation resistance value with the conductor having the plane electrically connected portion and the conductive liquid or another conductor electrically connected to the conductive liquid being as electrodes.

Still further, according to the present invention, there is provided a method of inspecting any crack in a ceramic substrate including a conductive film at least on one face, which comprises; disposing conductive liquid on the other face of the ceramic substrate, and measuring an insulation resistance value between both faces of the ceramic substrate or an electrically characteristic value which depends on the insulation resistance value with the conductive film and the conductive liquid or another conductor electrically connected to the conductive liquid being as electrodes.

The other conductor may be the whole or a part of a container containing the conductive liquid. Still further, the electrically characteristic value may be dielectric loss.

DETAILED DESCRIPTION OF THE PREFERRED EMBODIMENTS

Figure 1:
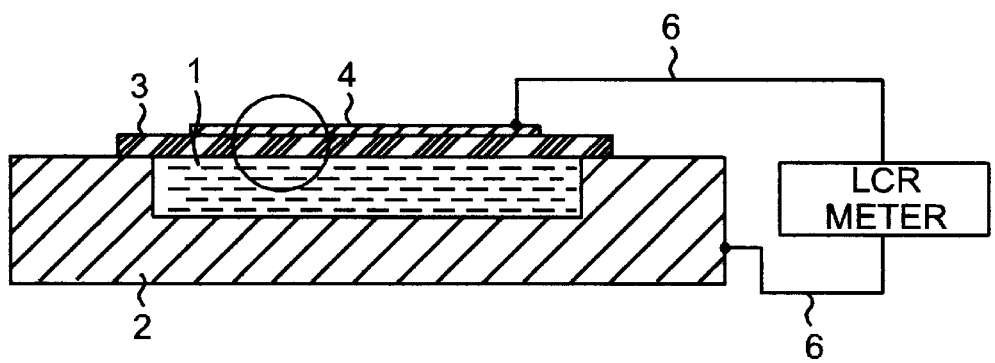
FIG. 1 is a view schematically showing an example of an inspection apparatus used in a method of inspection for a crack according to the present invention.

According to a method of inspection for a crack of the present invention, by disposing conductors on both faces of a ceramic substrate and by measuring an insulation resistance value or an electrically characteristic value which depends on the insulation resistance value with the conductors acting as the electrodes, a crack in the ceramic substrate is detected. Here, conductive liquid is used as at least one of the conductors.

Since liquid is used as at least one of the conductors, in case there is a crack, the conductive liquid soaks into the crack due to capillary phenomenon to come in contact with the conductor on the opposite face, thereby decreasing the insulation resistance value. On the contrary, in case there is no crack, the insulation resistance value does not change. Therefore, by using the conductive liquid, whether there is a crack or not can be grasped objectively and quantitatively.

The principle of the method of the present invention as mentioned in the above requires that at least a conductor on one face of the ceramic substrate is the liquid, but the conductor on the other face of the ceramic substrate is not necessarily required to be the liquid. However, in order to inspect efficiently whether there is a crack or not, it is preferable that the conductor disposed on the other face has a plane electrically connected portion which can be in close contact with the face of the ceramic substrate. Further, more preferably, a plane conductor having an area and a shape substantially similar to those of the ceramic substrate is used. Still further, if a plastic material is used as the conductor, it can also be applied to inspect of a bent ceramic substrate.

In case a conductive film is provided on one face or both faces of the ceramic substrate, the conductive film can be used as an electrode. Specifically, one of the electrodes is a conductive film provided on one face of the ceramic substrate while the other of the electrodes is a conductor formed of the conductive liquid disposed on the other face of the ceramic substrate. By measuring the insulation resistance value between the both faces in this way, a crack coated with the conductive film can be detected.

In the method of inspection for a crack of the present invention, another conductor electrically connected to the conductive liquid may be used as an electrode. For example, the whole or a part of a container containing the conductive liquid may be formed of a conductive material such that the container or the conductive portion of the container is used as an electrode.

It is preferable that the specific resistivity of the conductive liquid used in the present invention is small. Specifically, the specific resistivity is preferably 0–20 $\Omega \cdot m$, and is, more preferably, 0–2 $\Omega \cdot m$.

It is also preferable that the surface tension of the conductive liquid is small. Specifically, the surface tension is preferably 0–80 dyn/cm, and is, more preferably, 0–50 dyn/cm. If the surface tension is more than 80 dyn/cm, the wettability is so small that the capillary phenomenon is difficult to occur, thereby lowering the precision of detecting a crack.

The viscosity of the conductive liquid is preferable 0–1,000 mPa·s, and is, more preferably, 1–300 mPa·s. If the viscosity is more than 1,000 mPa·s, the fluidity of the liquid is so small that bubbles are likely to be contained therein.

Still further, it is preferable that the conductive liquid has a high washability and a low foamability. Further, a small amount of a defoaming agent such as alcohol may be added to the conductive liquid optionally. If the conductive liquid has a low washability, a component of the liquid may remain on the ceramic substrate, causing a stain or defective insulation. If the conductive liquid has a high foamability, bubbles between the conductive liquid and the ceramic substrate make the electric resistance large, thereby increasing noise in the measurement.

For the reasons mentioned in the above, as the conductive liquid used in the present invention, synthetic detergent, conductive coating, etc. are preferable, and in particular, synthetic detergent having a low foamability is preferable.

As the other materials electrically connected to the conductive liquid and, in case the conductive liquid is used only on one side of a ceramic substrate, as a material for the conductor disposed on the opposite side to the conductive liquid, Au, Ag, Pt, Cu, Al, SUS, etc. are used. Preferably, a material having a small specific resistivity is used.

Further, although an insulation resistance, a dielectric loss, Q (quality factor), etc. can be the electrically characteristic value which depends on the insulation resistance value, from the standpoint of simplicity and stability, it is preferable that dielectric loss is measured. Since the relationship between the insulation resistance value R and the value of dielectric loss D can be expressed as $D(\tan\delta)=1/\omega CR$, if there is a crack, the value of dielectric loss increases. Preferably, which of the electrically characteristic values is selected to judge whether there is a crack or not is appropriately decided taking into consideration the electric characteristics of the conductive liquid, the structure of the ceramic substrate to be inspected, etc.

Although it is preferable that the measured voltage when the dielectric loss is measured is in the range to which an ordinary LCR meter can be set, that is, from 5 mV to 2 V, around 1.0 V which is popularly used is sufficient.

Further, the measured frequency is preferably 100 Hz–100 kHz, and more preferably, 300 Hz–1 kHz.

The present invention is now described in more detail with reference to embodiments shown in the figures. However, the present invention should not be construed to be limited to these embodiments.

Example 1

Figure 2:
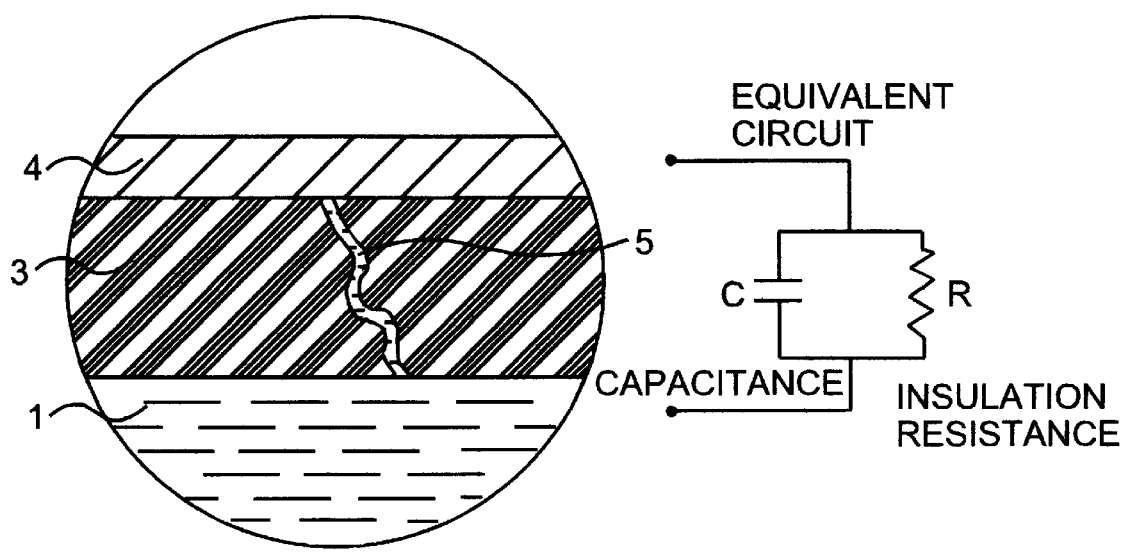
FIG. 2 is an enlarged view of the circled portion of FIG. 1.

According to the method of inspection for a crack of the present invention, measurement was conducted to inspect a ceramic substrate for a crack. FIG. 1 shows an inspection apparatus used in the measurement. FIG. 2 is an enlarged view of a part shown in FIG. 1.

In FIG. 1, a ceramic substrate 3 is mounted on a container 2 formed of a conductive metal filled with conductive liquid 1 such that a face of the ceramic substrate 3 that does not have a conductive film 4 is in contact with the liquid 1. The conductive film 4 and the container 2 are connected to an LCR meter via leads 6.

As shown in FIG. 2, if there is a crack, since the liquid 1 goes up through the crack 5 due to capillary phenomenon to come in contact with the conductive film 4, the liquid 1 is electrically connected to the conductive film 4 to decrease the insulation resistance value, thereby increasing the value of dielectric loss.

The inspection was made by measuring dielectric loss under the following conditions: the measured voltage was 1 V; the measured frequency was 1 kHz, the bias voltage was 0 V; and the specific resistivity, the wettability expressed as the surface tension, and the viscosity of the conductive liquid 1 were 1.0 $\Omega \cdot m$, 28.0 dyn/cm, and 50 mPa·s, respectively.

Examples 2–10

In the same way as in Example 1, measurement was conducted to inspect other ceramic substrates for a crack.

Figure 3:
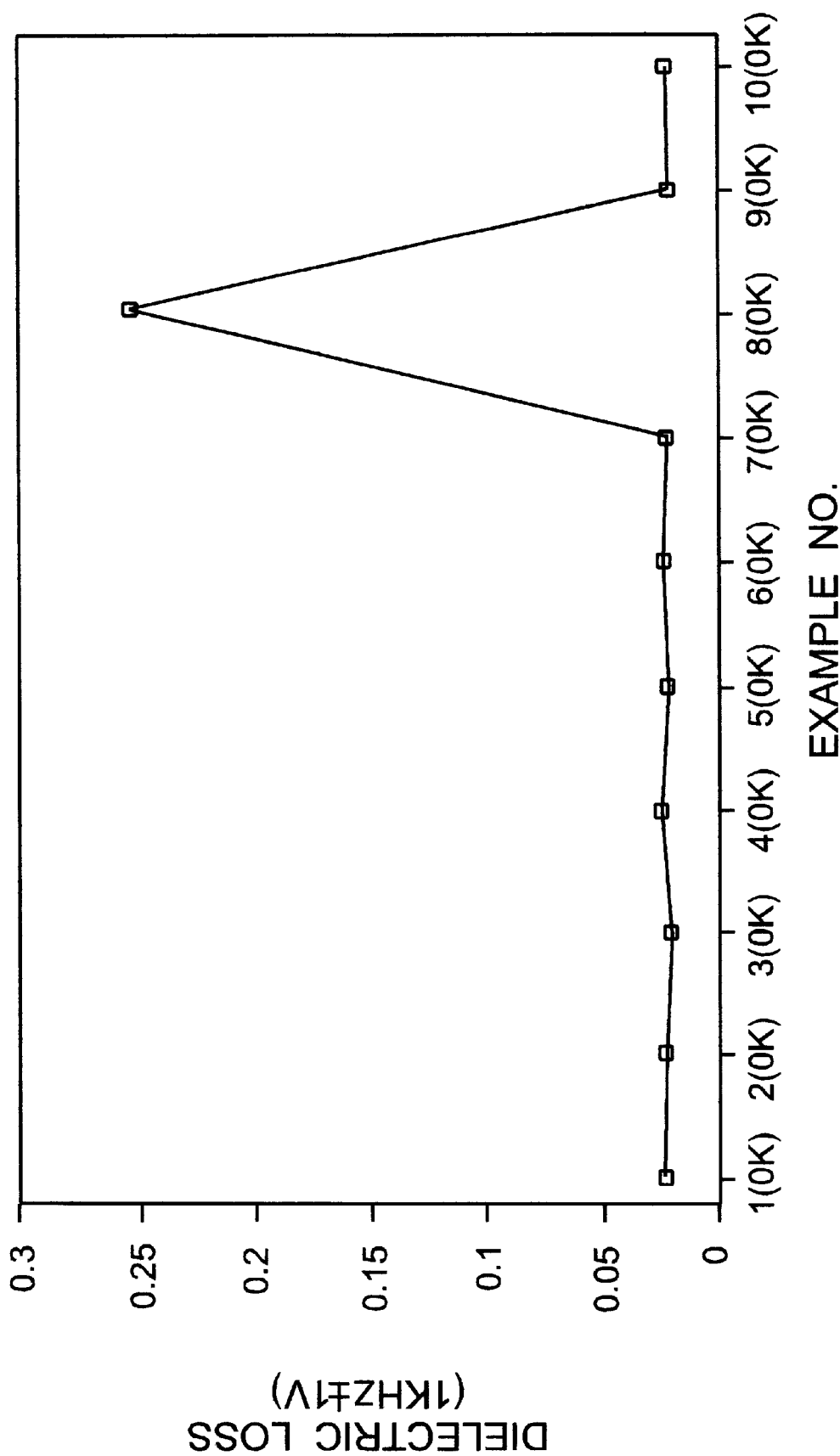
FIG. 3 is a graph showing results of measurement according to the method of inspection for a crack of the present invention.

FIG. 3 shows the results of the measurement in the inspection of the ceramic substrates for a crack. In addition, results of inspection according to the liquid penetrant test are put in parentheses in FIG. 3. "OK" means that the judgement was that there is no crack, while "NG" means that the judgement was that there is a crack.

Example 11

Figure 4:
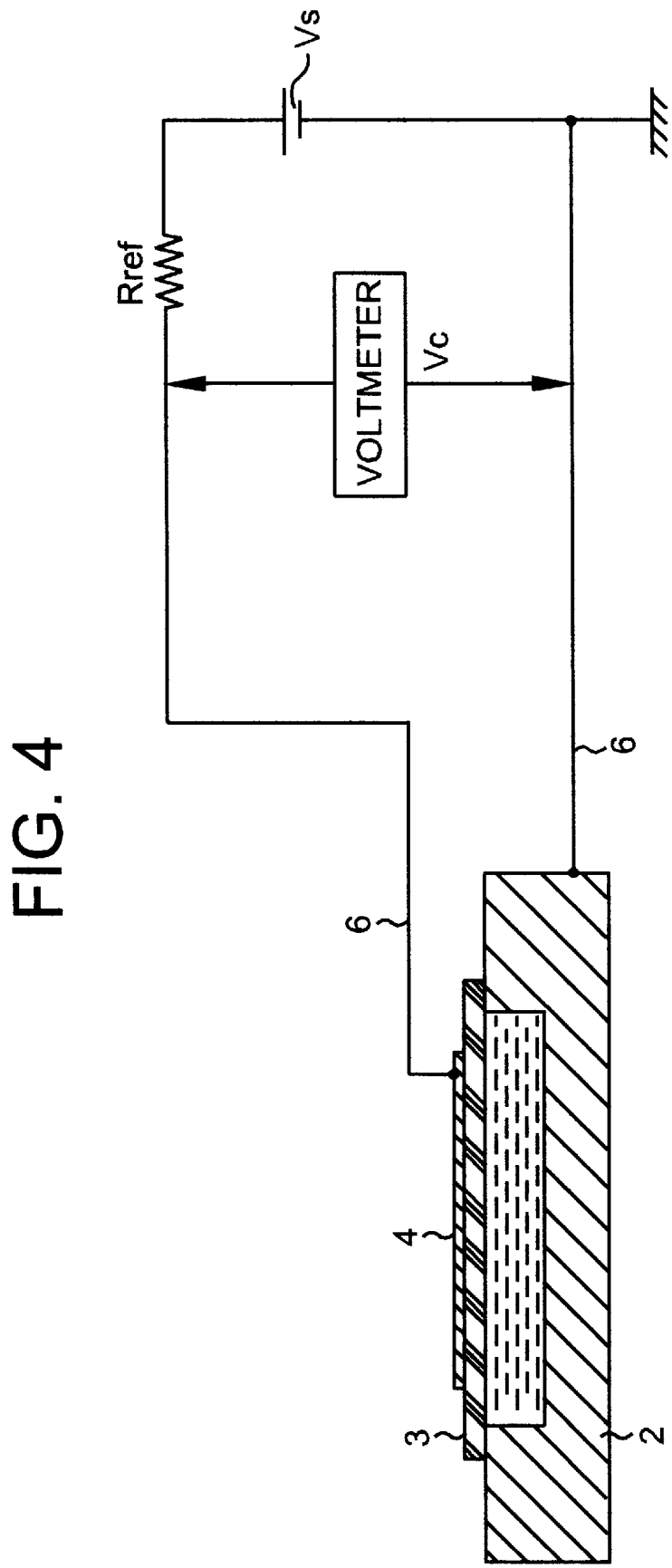
FIG. 4 is a schematic view showing another example of an inspection apparatus used in the method of inspection for a crack according to the present invention.

FIG. 4 shows another example of an inspection apparatus used in the method of inspection for a crack according to the present invention. In FIG. 4, the ceramic substrate 3 is connected in series to a reference resistance $R_{ref}$. Voltage $V_c$ of the ceramic substrate 3 when constant voltage $V_s$ is applied is measured. By calculating insulation resistance R of the ceramic substrate 3 according to the following equation:

$$R=(V_s-V_c)/V_c \times R_{ref}$$

a crack can be detected with simplicity.

As a result of the measurement in the inspection for a crack with the apparatus shown in FIG. 1 or FIG. 4 according to the method mentioned in the above, the same results as in the inspection according to the liquid penetrant test were obtained. Further, since it takes only several dozen msec to measure one sample, the efficiency of inspection was greatly improved compared with the liquid penetrant test.

By using the method of inspecting a ceramic substrate for a crack according to the present invention, even a crack which is coated with a conductive film and is not exposed on the surface of a ceramic substrate can be detected, a crack is not left undetected, and objective judgement is made possible since the result of inspection is expressed as numerical data. Further, since it takes only several dozen msec to measure one sample, mechanized and high-speed processing can be conducted.

What is claimed is:

1. A method of inspecting a crack in a ceramic substrate comprising the steps of:

disposing conductors on both faces of the ceramic substrate, one of the conductors being a conductive liquid and the other of the conductors having a plane electrically connected portion; and measuring by having said conductive liquid contact directly at least one surface of said ceramic substrate one of (i) an insulation resistance between the faces of the ceramic substrate and (ii) an electrical property dependent on the insulation resistance wherein the conductor having the plane electrically connected portion and one of the conductive liquid itself and a conductor electrically connected to the conductive liquid are used as electrodes.

2. A method of inspecting a crack in a ceramic substrate according to claim 1, wherein the conductor electrically connected to the conductive liquid is at least a part of a container containing the conductive liquid.

3. A method of inspecting a crack in a ceramic substrate according to claim 1, wherein the electrical property dependent on the insulation resistance is dielectric loss.

4. A method of inspecting a crack in a ceramic substrate according to claim 1, wherein said conductive liquid is provided in a liquid conductive bath over which said ceramic substrate to be inspected is placed and a further conductive material is applied to or is already present on said ceramic substrate.

5. A method of inspecting a crack in a ceramic substrate having a conductive film on at least one face thereof comprising the steps of:

disposing conductive liquid on the face of the ceramic substrate opposite the face having a conductive film thereon, and measuring by having said conductive liquid contact directly at least one surface of said ceramic substrate one of (i) an insulation resistance between the faces of the ceramic substrate and (ii) an electrical property dependent on the insulation resistance wherein the conductive film and one of the conductive liquid itself and a conductor electrically connected to the conductive liquid are used as electrodes.

6. A method of inspecting a crack in a ceramic substrate according to claim 5, wherein the conductor electrically connected to the conductive liquid is at least a part of a container containing the conductive liquid.

7. A method of inspecting a crack in a ceramic substrate according to claim 5, wherein the electrical property dependent on the insulation resistance is dielectric loss.

* * * * *